(12) United States Patent
Juretich et al.

(10) Patent No.: US 10,080,836 B2
(45) Date of Patent: Sep. 25, 2018

(54) ABSORPTION-BASED OPTICAL SENSOR FOR DETECTING INFUSION PUMP CASSETTE

(71) Applicant: Zevex, Inc., Salt Lake City, UT (US)

(72) Inventors: Jeffery T. Juretich, Herriman, UT (US); Michael Marshall, Herriman, UT (US); Michael Elwood, Farmington, UT (US)

(73) Assignee: Zevex, Inc., Salt Lake City, UT (US)

( * ) Notice: Subject to any disclaimer, the term of this patent is extended or adjusted under 35 U.S.C. 154(b) by 875 days.

(21) Appl. No.: 14/161,839

(22) Filed: Jan. 23, 2014

(65) Prior Publication Data

US 2015/0202384 A1 Jul. 23, 2015

(51) Int. Cl.
*A61M 5/00* (2006.01)
*A61M 5/142* (2006.01)

(52) U.S. Cl.
CPC ..... *A61M 5/14232* (2013.01); *A61M 2205/12* (2013.01); *A61M 2205/14* (2013.01); *A61M 2205/3306* (2013.01); *A61M 2205/70* (2013.01)

(58) Field of Classification Search
CPC .......... A61M 2205/14; A61M 2205/12; A61M 2205/121
See application file for complete search history.

(56) References Cited

U.S. PATENT DOCUMENTS

| | | | |
|---|---|---|---|
| 4,878,896 A | * | 11/1989 | Garrison ............... A61M 5/142 128/DIG. 12 |
| 5,514,102 A | | 5/1996 | Winterer et al. |
| 5,720,721 A | | 2/1998 | Dumas et al. |
| 6,094,292 A | * | 7/2000 | Goldner .................... E06B 9/24 359/265 |
| 6,523,414 B1 | | 2/2003 | Malmstrom et al. |
| 6,531,708 B1 | | 3/2003 | Malmstrom et al. |
| 6,852,094 B2 | | 2/2005 | Beck et al. |
| 7,560,686 B2 | | 7/2009 | Bisch et al. |
| 7,722,562 B2 | | 5/2010 | Hanlon et al. |
| 7,722,573 B2 | | 5/2010 | Harr et al. |

(Continued)

FOREIGN PATENT DOCUMENTS

| | | |
|---|---|---|
| EP | 1839690 | 10/2007 |
| EP | 2399626 | 12/2011 |

(Continued)

*Primary Examiner* — Edelmira Bosques
(74) *Attorney, Agent, or Firm* — Hodgson Russ LLP

(57) ABSTRACT

An infusion pump has an optical cassette detection system for determining whether or not a cassette of an administration tubing set is properly loaded in the pump. Operation of the pump may be enabled or disabled based on a determination of the cassette detection system. The cassette detection system includes a light emitter and a corresponding photosensitive detector aligned along an optical axis, and window carried by the cassette. When the cassette is properly loaded in the pump, a light beam from the emitter enters the window, where a portion of the beam is absorbed and another portion of the beam is transmitted for receipt by the detector. The detector signal is evaluated by signal evaluation electronics to determine if the cassette is loaded. The determination may be based on an expected attenuation of the light beam corresponding to a predetermined light absorptance property of the window.

6 Claims, 4 Drawing Sheets

(56) References Cited

U.S. PATENT DOCUMENTS

| | | |
|---|---|---|
| 7,758,551 B2 | 7/2010 | Wiesner et al. |
| 7,762,989 B2 | 7/2010 | Simpson |
| 7,763,005 B2 | 7/2010 | Knauper et al. |
| 7,927,304 B2 | 4/2011 | Hudson et al. |
| 8,021,336 B2 | 9/2011 | Boulanger et al. |
| 8,052,642 B2 | 11/2011 | Harr et al. |
| 8,052,643 B2 | 11/2011 | Hudson et al. |
| 8,053,721 B2 | 11/2011 | Bisch et al. |
| 8,142,399 B2 | 3/2012 | Hanlon et al. |
| 8,142,404 B2 | 3/2012 | Knauper et al. |
| 8,529,511 B2 | 9/2013 | Boulanger et al. |
| 8,679,075 B2 | 3/2014 | Lurvey et al. |
| 2006/0129104 A1* | 6/2006 | Cowan ............... A61M 5/1452 604/181 |
| 2007/0208307 A1* | 9/2007 | Knauper ........... A61M 5/14212 604/131 |
| 2013/0030405 A1 | 1/2013 | Hartman et al. |

FOREIGN PATENT DOCUMENTS

| | | |
|---|---|---|
| JP | H02140173 A | 5/1990 |
| JP | 2005506852 A | 3/2005 |
| JP | 2008537491 A | 9/2008 |
| JP | 2011200326 | 10/2011 |

\* cited by examiner

ABSORPTION-BASED OPTICAL SENSOR FOR DETECTING INFUSION PUMP CASSETTE

FIELD OF THE INVENTION

The present invention relates generally to infusion pumps for controlled delivery of liquid food and medications to patients. More specifically, the present invention relates to a sensor system in an infusion pump for detecting the presence or absence of a cassette by which an administration tubing set is operatively connected to the pump.

BACKGROUND OF THE INVENTION

Programmable infusion pumps are used to carry out controlled delivery of liquid food for enteral feeding and medications for various purposes, for example pain management. In a common arrangement, an infusion pump receives a disposable administration set comprising a cassette removably received by the pump and flexible tubing connected to the cassette for providing a fluid delivery path through the pump.

The cassette itself may be intended for use with a particular infusion pump model or models, and/or with tubing having predetermined properties. In this regard, the cassette may include safety features that are designed and manufactured according to specifications determined at least in part by the intended infusion pump model and/or administration set tubing. The safety features of the cassette may cooperate with corresponding features on the matching pump, and may be manufactured according to size tolerances related to tubing diameter and flexibility. For example, the cassette may have an anti-free flow mechanism for protecting the patient from uncontrolled fluid delivery. The anti-free flow mechanism may take the form of an external pinch clip occluder actuated when the cassette is properly loaded in the pump and a door of the pump is closed. Alternatively, the anti-free flow mechanism may take the form of an internal "in-line occluder" that resides within the flow passage of the tubing, wherein a flow passage is only opened when the cassette is properly loaded in the pump and the pump door is closed.

The cassette may provide additional safety features beyond free flow protection. For example, the cassette may be matched to the pump to maintain a desired volumetric accuracy of the pump, and to ensure correct function of occlusion and air-in-line sensors used to trigger safety alarms.

In view of the safety importance of the cassette, it is desirable to provide means to detect whether or not a matching cassette is properly loaded in the pump as a precondition to enabling pump operation.

SUMMARY OF THE INVENTION

In accordance with the present invention, an infusion pump in which an administration set is removably received is provided with an optical detection system for determining whether or not a cassette of the administration set is properly loaded in the pump. In an embodiment of the present invention, operation of the pump is disabled if a cassette is not properly loaded in the pump.

The optical cassette detection system comprises an optical emitter mounted to the pump and arranged to emit a light beam directed along an optical axis, and a photosensitive detector mounted to the pump and arranged to receive the light beam along the optical axis. The cassette detection system further comprises a window carried by the cassette. The window is arranged to intersect the optical axis at a location between the optical emitter and the photosensitive detector when the cassette is properly loaded in the pump. The window absorbs a portion of the light beam and transmits another portion of the light beam. The transmitted portion of the light beam is received by the photosensitive detector. The photosensitive detector generates a detector signal representing an intensity of light received thereby.

The detector signal is evaluated by signal evaluation electronics to determine if the detector signal level is within an expected range, indicating presence of the cassette. The signal evaluation electronics may be in communication with a pump controller, wherein the pump controller is programmed to disable pump operation unless a cassette is present as determined by the optical cassette detection system.

The window may be made to have a predetermined absorptance with respect to a wavelength band of the light beam. In the context of the present specification, and as understood by persons skilled in the art of optical systems, "absorptance" means the ratio of the absorbed radiant or luminous flux to the incident radiant or luminous flux. By way of illustrative example, a window having an absorptance of 60% will absorb 60% of the beam energy and transmit the remaining 40% of the beam energy. Where the window has a known predetermined absorptance, the signal evaluation electronics can check for an expected attenuation indicated by reduction in the detector signal level from before a cassette is loaded to after a cassette is loaded.

In an embodiment of the invention, the window includes a light entry surface and a light exit surface parallel to the light entry surface, and the window is integrally formed with the cassette in a one-piece molded part made of transparent plastic or translucent plastic. The thickness of the window from light entry surface to light exit surface may be controlled, and the plastic may be doped with a constituent, to achieve a predetermined absorptance.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
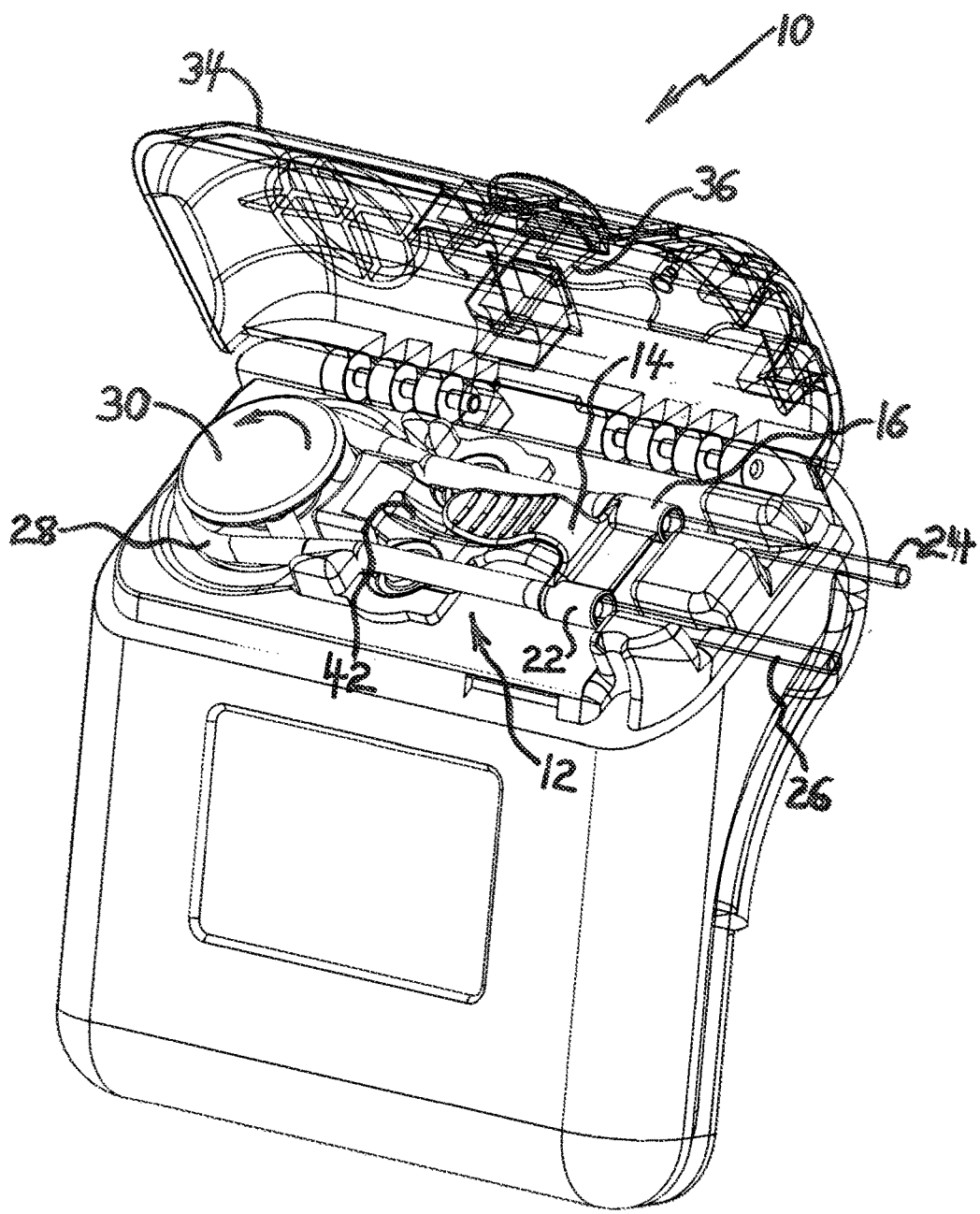
FIG. 1 is perspective view of an infusion pump and cassette incorporating a cassette detection system in accordance with an embodiment of the present invention.
Figure 2:
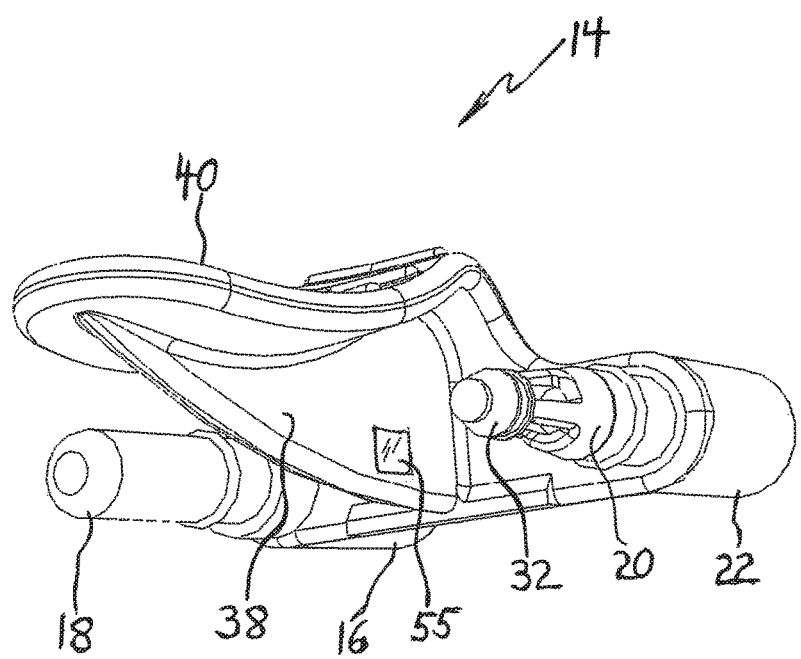
FIG. 2 is a perspective view of the cassette shown in FIG. 1.

FIG. 1 shows an infusion pump 10 in which an administration set 12 is removably received. Administration set 12 includes a cassette 14, which is shown by itself in FIG. 2. Cassette 14 may include an input connector 16, an upstream loop connector 18 in flow communication with input connector 16, a downstream loop connector 20, and an output connector 22 in flow communication with downstream loop connector 20. Administration set 12 may further include inflow tubing 24 having one end mated to input connector 16 and an opposite end (not shown) connected to a fluid source, and outflow tubing 26 having one end connected to output connector 22 and an opposite end (not shown) connected to a patient. Finally, administration set 14 may further include a pumping segment of tubing 28 having one end mated to upstream loop connector 18 and an opposite end mated to downstream loop connector 20.

In the illustrated embodiment, pump 10 is a rotary peristaltic pump having a rotor 30, wherein pumping segment 28 is wrapped around rotor 30 and is engaged by angularly spaced rollers on rotor 30 as the rotor rotates to provide peristaltic pumping action forcing liquid through the tubing of administration set 12. As may be understood by reference to FIG. 1, when rotor 30 rotates in a counter-clockwise direction, liquid is moved from inflow tubing 24 through input connector 16 and upstream loop connector 18 to pumping segment 28, and then from pumping segment 28 through downstream loop connector 20 and output connector 22 to outflow tubing 26. Although the present invention is described in the context of a rotary peristaltic pump, the invention is not limited to this type of infusion pump. The invention may be practiced with any type of infusion pump that receives an administration set having a cassette.

Cassette 14 may include an in-line occluder 32 which may be incorporated into downstream loop connector 20. In-line occluder 32 prevents flow when pump door 34 is open. An actuator 36 on an underside of pump door 34 engages pumping segment 28 in a manner which opens a flow path around occluder 32 when door 34 is closed.

Figure 3A:
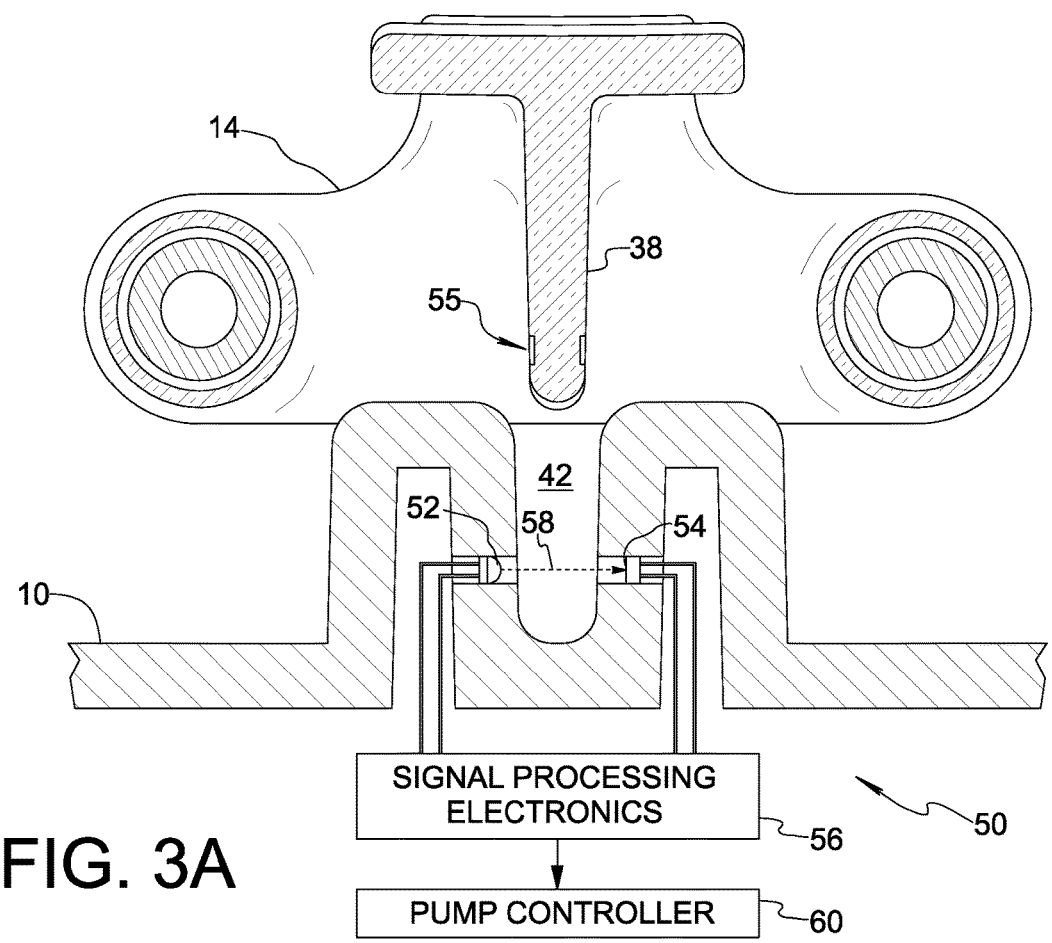
FIG. 3A is a schematic sectional view illustrating a cassette detection system formed in accordance with an embodiment of the present invention, wherein a tab of the cassette is shown prior to insertion into a tab-receiving slot of the pump.
Figure 3B:
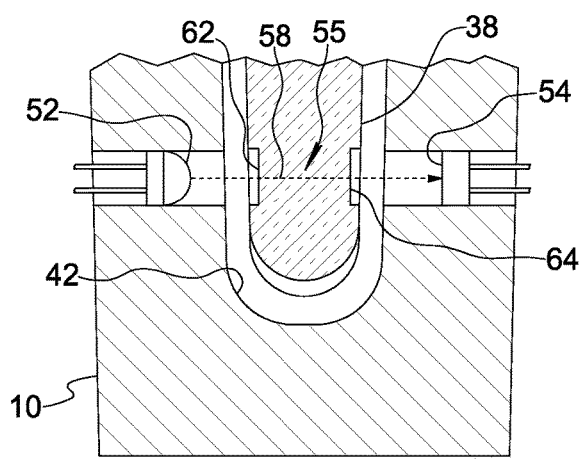
FIG. 3B is an enlarged view corresponding to FIG. 3A, however the cassette tab is shown inserted into the pump slot.

Reference is now made to FIGS. 3A and 3B. Cassette 14 includes a tab 38 depending downwardly from a ribbed thumb portion 40 of the cassette. In the present embodiment, tab 38 is a generally planar tab that is sized for receipt within a corresponding slot 42 in pump 10. Slot 42 may be provided at a location on pump 10 between the upstream and downstream portions of pumping segment 28, and tab 38 may be provided on an underside of thumb portion 40. For example, slot 42 may be midway between the upstream and downstream portions of pumping segment 28 and may be elongated in a direction aligned with the rotation axis of rotor 30, and tab 38 may be midway between one side of cassette 14 having input connector 16 and upstream loop connector 18 and the other side of cassette 14 having downstream loop connector 20 and output connector 22. In this symmetrical arrangement, cassette 14 is easily centered in pump 10 relative to rotor 30 during installation of administration set 12. In an embodiment of the invention, the width of slot 42 is 2.6 mm and the width of tab 38 is 1.7 mm.

Pump 10 includes an optical cassette detection system 50 operable to detect whether or not cassette 14 is properly loaded in pump 10 with cassette tab 38 present in slot 42. Cassette detection system 50 includes an optical emitter 52, which may be mounted to pump 10 on one side of slot 42, and a photosensitive detector 54, which may be mounted to pump 10 on an opposite side of slot 42. In the illustrated embodiment, detector 54 is aligned with emitter 52 along an optical axis 58 passing through slot 42. Detector 54 generates a signal, for example a current or voltage signal, having a level corresponding to the intensity of light received by the detector. Cassette detection system 50 further includes a window 55 carried by cassette 14. In accordance with the present invention, window 55 is arranged on cassette 14 to intersect optical axis 58 at a location between optical emitter 52 and photosensitive detector 54 when cassette 14 is properly loaded in pump 10. In the embodiment shown herein, emitter 52 and photosensitive detector 54 are each mounted in pump 10 adjacent to slot 42, and window 55 is part of tab 38, however other configurations and arrangements are possible.

Cassette detection system 50 may also include signal processing electronics 56 connected to photosensitive detector 54 for receiving an electronic signal generated by detector 54 and evaluating the signal. Signal processing electronics 56 may be in communication with a pump controller 60, whereby operation of pump 10 may be controlled based on an evaluation of the detector signal.

As best seen in FIG. 3B, window 55 may include a light entry surface 62 normal to optical axis 58, and a light exit surface 64 also normal to optical axis 58. Window 55 may be integrally formed with tab 38 or with cassette 14 as a whole, wherein surfaces 62 and 64 are formed as external surface features of the molded part. For example, cassette 14 may be molded from transparent or translucent optical grade plastic that is doped with a constituent or otherwise provided with a desired absorptivity (internal absorptance per unit length). Possible doping constituents include, but are not limited to, ROMBEST® HT 555, VIBATAN® PE IR Absorber 00535, and Polytechs IR 67. The thickness of window 55 from entry surface 62 to exit surface 64 may be specified in conjunction with the absorptivity of the window material to achieve a desired absorptance value for window 55 as a whole.

When cassette 14 is not loaded in pump 10, the light beam from emitter 52 passes directly to detector 54 with negligible beam attenuation because window 55 is not present. As a result, detector 54 generates a relatively high signal level, referred to herein as a "baseline signal," when cassette 14 is not loaded. When cassette 14 is properly loaded in pump 10, window 55 absorbs a portion of the light beam from emitter 52 and transmits another portion of the light beam. As will be understood, the transmitted portion of the light beam is received by photosensitive detector 54. Consequently, when cassette 14 is loaded in pump 10, the level of the signal generated by detector 54 is reduced somewhat relative to the baseline signal.

Window 55 may have a predetermined absorptance with respect to a wavelength band of the light beam that is greater than 0% (no absorption) and less than 100% (complete absorption). The baseline detector signal will be reduced according to a predetermined ratio by properly loading cassette 14 in the infusion pump 10, wherein the predetermined ratio is greater than 0% and less than 100%. The predetermined ratio may correspond to the predetermined absorptance of window 55 in one of two ways. First, if dark current and noise are eliminated from the detector signal by system calibration such that the entire detector signal varies proportionally with changes in the intensity of received light, then the reduction ratio will correspond directly with the absorptance of window 55. For example, if the absorptance of window 55 is 75%, then a 75% reduction in the detector signal level relative to the baseline signal level is expected. Second, if dark current and noise are not eliminated from the detector signal such that the detector signal has a fixed component that does not vary proportionally with changes in the intensity of received light and a variable component that does vary proportionally with changes in the intensity of received light, then only the variable component of the detector signal will be reduced by introduction of window 55. In this latter case, the reduction ratio will correspond indirectly with the absorptance of window 55 according to the following relation:

REDUCTION RATIO=ABSORPTANCE×((BASELINE−DARK)/BASELINE)

For example, if the detector signal has a fixed level of 20 units under dark conditions and a baseline level of 100 units, and the absorptance of window 55 is 75%, then loading of the cassette will cause an expected reduction of the signal level from 100 units down to 40 units. In this example, the overall reduction ratio is 60% and corresponds indirectly with the window absorptance, taking into account a fixed dark signal component. Under either scenario, a predictable reduction in the detector signal is associated with proper loading of cassette 14.

Figure 4:
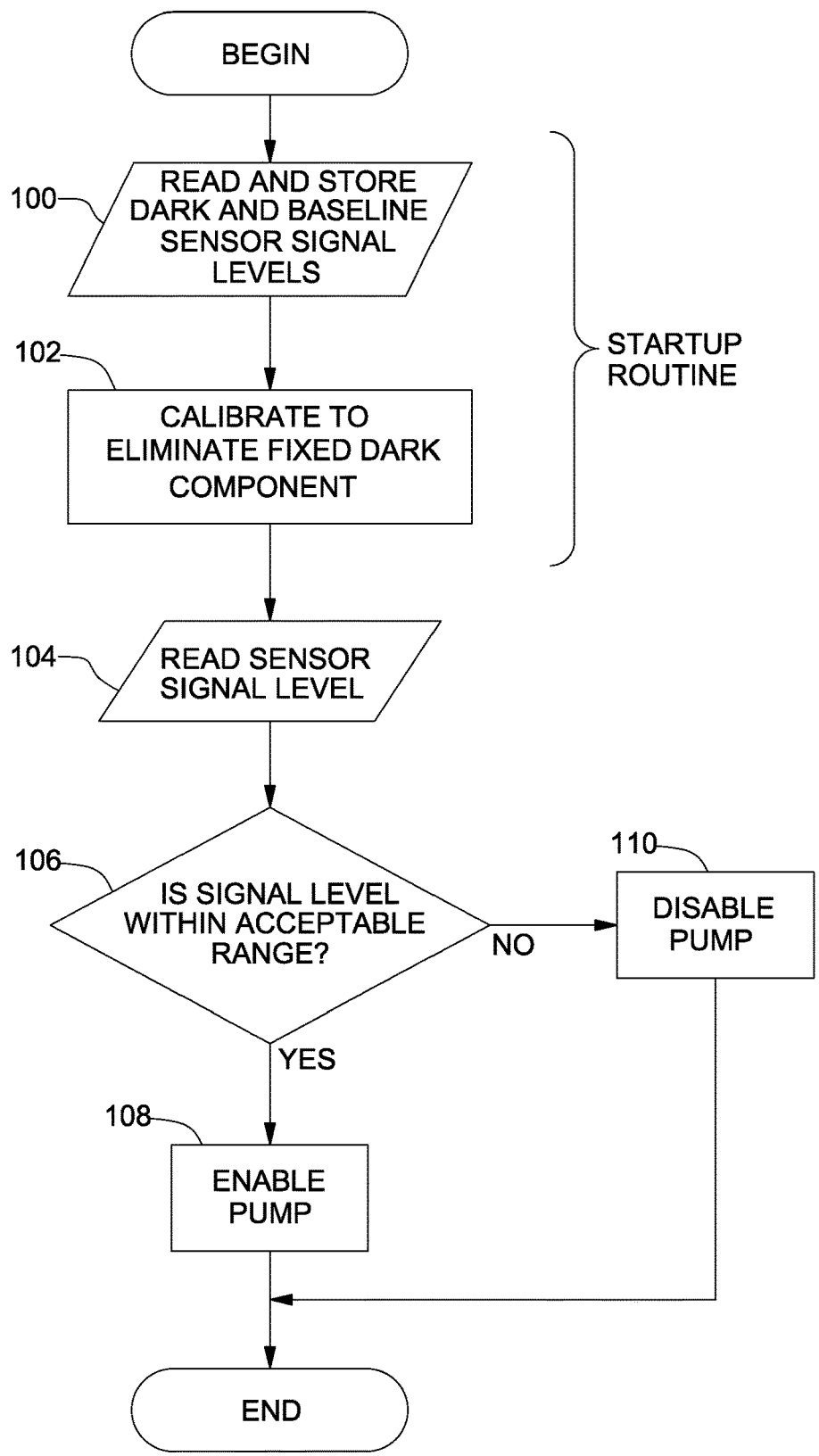
FIG. 4 is a flow diagram showing decision logic executed by the cassette detection system in accordance with an embodiment of the present invention.

Signal processing electronics 56 evaluates the signal from detector 54 to determine if cassette 14 is properly loaded in pump 10. The signal processing and evaluation may be completely analog, or the detector signal level may be converted to a digital value and compared to a threshold in a digital comparator circuit. As illustrated in FIG. 4, operation of pump 10 may be enabled or disabled based on the determination made by signal processing electronics 56.

In block 100, a routine is executed at pump startup to read and store the signal level of detector 54 when there is no cassette loaded and emitter 52 is OFF (the so-called "dark" of fixed detector signal level), and to read and store the baseline signal level of detector 54 when there is no cassette loaded and emitter 52 is ON. A calibration of the detector signal may be executed as part of the startup routine as indicated by block 102 to eliminate effects of the fixed dark signal component. After startup, the level of the detector signal is read in block 104 to ascertain loading of a cassette. In block 106, the signal level may be evaluated to determine if it is in an acceptable range based on the predetermined baseline signal level and the absorptance of window 55. For example, if the baseline signal is 100 units and the expected reduction ratio directly corresponds to a window absorptance of 75%, then the acceptable range may be a range that includes 25 units plus or minus a variability tolerance, for example plus or minus 5 units. Under this example, the acceptable signal level range would be from 20 units to 30 units. If the measured signal level falls in the acceptable range, proper loading of a cassette is indicated and flow branches to block 108, wherein pump operation is enabled by pump controller 60. However, if the signal level is outside of the acceptable range, flow branches to block 110 and pump operation is disabled by pump controller 60.

Emitter 52 may be a light-emitting diode (LED) or other light source, and photosensitive detector 54 may be a photodiode or other photosensitive element capable of generating an electrical signal in response to incident light. Emitter 52 and detector 54 may be chosen to operate within predetermined wavelength bands. For example, where window 55 is made to absorb light in an infrared wavelength band, emitter 52 may be chosen to emit light in that infrared band, and detector 54 may have a spectral responsivity substantially confined to that infrared band. Alternatively, emitter 52 may be a narrow band emitter, for example a laser diode. Likewise, detector 54 may have a spectral responsivity across a relatively wide wavelength band that includes the emission wavelength band. Emitter 52 and detector 54 may be optically coupled by light outside the visible spectrum, e.g. infrared or ultraviolet light. While not shown, emitter 52 and detector 54 may have lenses, fiber optics, or other optical elements associated therewith for collimating, focusing, and/or directing the beam.

Tab 38 on cassette 14 provides structure that may be used for carrying window 55 and positioning the window in optical cassette detection system 50. A wide variety of tab arrangements and optical detection system configurations are of course possible. The centered arrangement of a thin tab 38 on the underside of cassette 14, and the use of a thin slot 42 in pump 10, takes advantage of the tab and slot as a means for guiding and centering the cassette 14 during installation. Moreover, the cassette detection system 50 is hidden within the pump and is inconspicuous to users. Emitter 52 and detector 54 may be recessed slightly from the surface of slot 42 behind respective transparent barriers (not shown) to keep dirt and fluid away from the emitter and detector.

While the invention has been described in connection with exemplary embodiments, the detailed description is not intended to limit the scope of the invention to the particular forms set forth. The invention is intended to cover such alternatives, modifications and equivalents of the described embodiment as may be included within the spirit and scope of the invention.

What is claimed is:

1. A cassette (14) to be loaded in an infusion pump for operatively connecting an administration set to the pump, the cassette (14) comprising:
   an input tubing connector (16);
   an upstream loop tubing connector (18) in flow communication with the input tubing connector (16) to define a first flow path through the cassette;
   a downstream loop tubing connector (20);
   an output tubing connector (22) in flow communication with the downstream loop tubing connector (20) to define a second flow path through the cassette; and
   a tab (38) located between the first flow path and the second flow path, the tab (38) including a window (55) having a predetermined absorptance greater than 0% and less than 100% with respect to a known wavelength band of light;
   wherein the window (55) has a light entry surface (62) and a light exit surface (64) on opposite sides of the tab (38), wherein the light entry surface (62) and the light exit surface (64) are external surface features of the cassette (14), and neither the first flow path nor the second flow path is located between the light entry surface (62) and the light exit surface (64) of the window (55).

2. The cassette according to claim 1, wherein the light exit surface (64) is parallel to the light entry surface (62).

3. The cassette according to claim 2, wherein the predetermined absorptance of the window (55) is defined by a thickness of the window (55) from the entry surface (62) to the exit surface (64) and an absorptivity of material forming the window (55).

4. The cassette according to claim 1, wherein the cassette is a one-piece molded part.

5. The cassette according to claim 4, wherein the cassette is molded from translucent plastic.

6. The cassette according to claim 4, wherein the cassette is molded from transparent plastic doped with a constituent.

* * * * *